United States Patent
Lamirey

(10) Patent No.: US 6,913,478 B2
(45) Date of Patent: Jul. 5, 2005

(54) MULTI-CONTACT CONNECTOR FOR ELECTRODE FOR EXAMPLE FOR MEDICAL USE

(75) Inventor: Marc Lamirey, Vy le Ferroux (FR)

(73) Assignee: Dixi Microtechniques, S.A., Besancon (FR)

( * ) Notice: Subject to any disclaimer, the term of this patent is extended or adjusted under 35 U.S.C. 154(b) by 0 days.

(21) Appl. No.: 10/602,778

(22) Filed: Jun. 24, 2003

(65) Prior Publication Data
US 2004/0005802 A1 Jan. 8, 2004

(30) Foreign Application Priority Data
Jul. 1, 2002 (FR) ............................................. 02 08186

(51) Int. Cl.$^7$ ............................................. H01R 13/15
(52) U.S. Cl. ....................... 439/259; 439/909; 439/668; 600/486; 600/378; 607/37
(58) Field of Search ................................ 439/668, 669, 439/259, 263, 909; 607/37, 115, 486, 378; 600/486, 378

(56) References Cited

U.S. PATENT DOCUMENTS

| | | | |
|---|---|---|---|
| 3,222,471 A | | 12/1965 | Steinkamp |
| 5,766,042 A | * | 6/1998 | Ries et al. .................... 439/668 |
| 6,044,302 A | * | 3/2000 | Persuitti et al. ................ 607/37 |
| 6,112,120 A | * | 8/2000 | Correas ........................ 607/37 |
| 6,162,101 A | | 12/2000 | Fischer et al. |
| 6,192,278 B1 | | 2/2001 | Werner et al. |
| 6,415,168 B1 | * | 7/2002 | Putz ............................ 600/378 |
| 6,428,336 B1 | * | 8/2002 | Akerfeldt .................... 439/263 |
| 6,439,932 B1 | * | 8/2002 | Ripolone .................... 439/668 |
| 6,663,570 B2 | * | 12/2003 | Mott et al. ................... 600/486 |
| 6,671,554 B2 | * | 12/2003 | Gibson et al. ................ 607/37 |
| 6,725,096 B2 | * | 4/2004 | Chinn et al. ................. 607/115 |

FOREIGN PATENT DOCUMENTS

EP 1147783 10/2001

\* cited by examiner

Primary Examiner—Gary Paumen
(74) Attorney, Agent, or Firm—Davis & Bujold, P.L.L.C.

(57) ABSTRACT

Multiple contact connector for an electrode, for example, for medical use.

The present invention relates to a multiple contact connector with reduced space requirement and weight regardless of the number of electrical contacts of the electrode, which can receive one or two electrodes, which guarantees a reliable and secured electrical connection with no risk of accidental disconnection and which is not a problem for a patient in whom the electrodes are implanted.

This connector (1) consists of male plug (6) which has elongated support (60) provided on at least one of its sides with a number of contact zones (61) equal to the number of contacts of said electrode (2) and which are aligned parallel to the axis of first cable section (4), and female socket (7) having roughly cylindrical body (70) arranged in the extension of second cable section (5) and having at least one housing (71) provided with a number of contact elements (72) equivalent to the number of contact zones (61) of said male plug (6) and capable of receiving said support (60). This connector (1) is characterized in that it has tightening sleeve (8) arranged in order to maintain support (60) in housing (71) and to exert a radial pressure of contact zones (61) on contact elements (72) in such a way as to ensure the electrical connections.

22 Claims, 5 Drawing Sheets

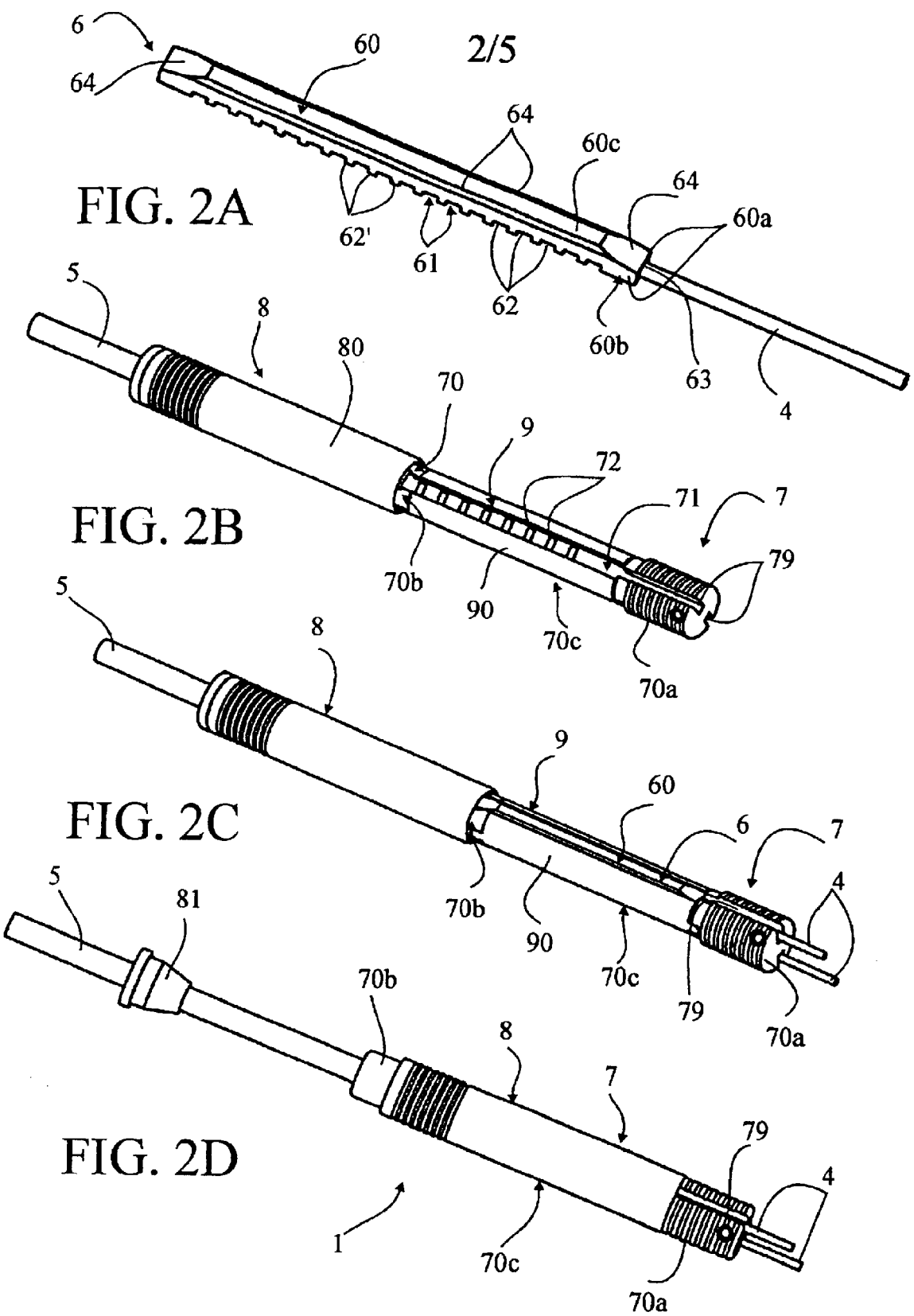

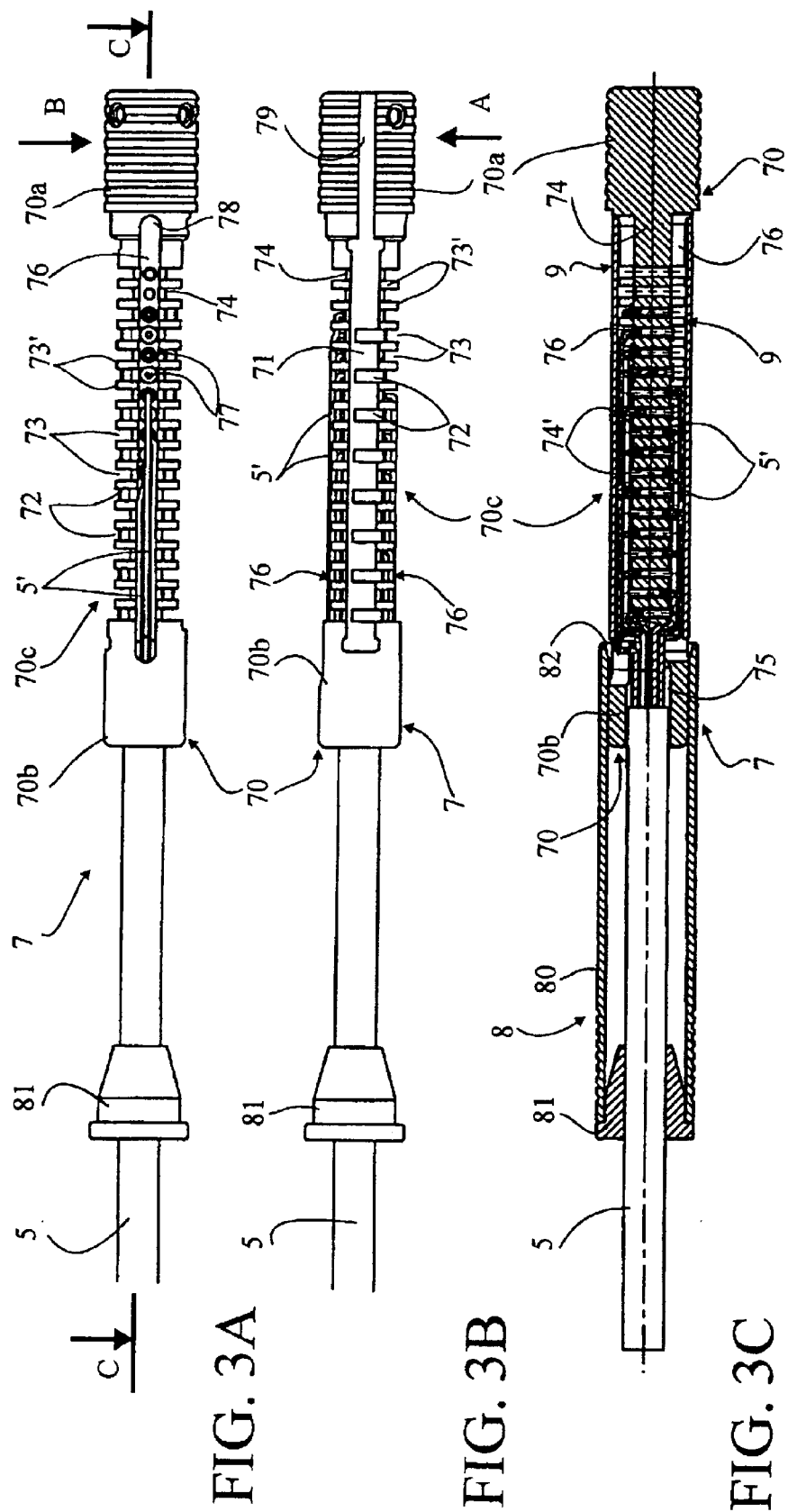

MULTI-CONTACT CONNECTOR FOR ELECTRODE FOR EXAMPLE FOR MEDICAL USE

This application claims foreign priority under 35 U.S.C. §119 of French Patent Application FR 02/08186 filed Jul. 1, 2002.

FIELD OF THE INVENTION

The present invention relates to a multiple contact connector for an electrode, for example, for medical use.

BACKGROUND OF THE INVENTION

Multiple contact electrodes are used in various applications and particularly in the medical domain, for example, in functional and stereotactic neurosurgery. These electrodes are, for example, implanted on a patient near or directly in the zones which are to be monitored, stimulated and/or treated, such as the brain, the spinal cord, etc. They are, for example, used in the treatment of certain diseases such as epilepsy, anorexia, Parkinson's disease, but also in the treatment of certain cancers. They are present in the form of fine needles or flat screens which have several electrical contacts in the form of peripheral rings or pads. They are coupled with recording and/or stimulation and/or treatment apparatuses by multiconductor cables and multiple contact connectors which can be plugged in according to a plane roughly perpendicular to the cables. Each connector is formed by a male plug and a female socket. The male plug is connected to an electrode by a multiconductor cable and has the same number of pins as the number of electrical contacts, these pins being parallel to one another. Each female socket is part of an adaptor or extension cord formed by a multiconductor cable, and has, on the side of the male plug, the same number of tubes as the number of electrical contacts, these tubes being parallel to one another, and on the side of the apparatus, the same number of DIN plugs as the number of tubes.

These traditional connectors, such as those described in the publications EP-A-1 147 783 and U.S. Pat. No. 3,222,471, have an approximately cubical shape whose transverse dimension depends on the number of contacts of the electrode. Moreover, one needs the same number of connectors as the number of electrodes implanted. The angular shape and the large space requirement of these connectors are particularly problematic for the patient since they are arranged in his nearby environment. They consequently generate a non-negligible weight which exerts traction on the multiconductor cables and on the electrodes, and hinder the movements of the patient. Moreover, during his movements, the patient may accidentally unplug the connectors, threatening his treatment and/or his monitoring. Furthermore, in order to implant electrodes precisely, guide cannulas are used, which must be extracted from the electrode by the rear end of the multiconductor cable. The presence of the rectangular male plug constitutes an obstacle and does not allow the use of these cannulas.

SUMMARY OF THE INVENTION

The present invention aims to address these disadvantages by proposing a multiple contact connector with reduced space requirement and weight regardless of the number of electrical contacts of the electrode, which is therefore better accepted by the patient, which can receive one or two electrodes, which allows the use of guide cannulas, and which guarantees a reliable and secured electrical connection with no risk of accidental disconnection.

For this purpose, the invention relates to a multiple contact connector of the type which has at least one so-called male plug which is intended to be connected to a multiple contact electrode by a first section of multiconductor cable and a so-called female socket provided at the end of a second section of multiconductor cable which is intended to electrically connect said electrode to an apparatus for processing of the electrical signals of said electrode the male plug having an elongated, electrically insulating support arranged in the extension of the first cable section and provided on at least one of its sides with a number of contact zones equal to the number of contacts of said electrode, these contact zones being aligned according to a line which is roughly parallel to the axis of said first cable section, the female socket having an elongated, electrically insulating body arranged in the extension of the second cable section, this body having at least one longitudinal housing, roughly parallel to the axis of said second cable section, provided with a number of contact elements equal to the number of contact zones of said male plug and capable of receiving said support in such a way that each contact zone is arranged facing a contact element characterized in that it has some means of tightening arranged in order to maintain said support in the housing of said body and to exert a radial pressure of the contact zones on the contact elements in such a way as to ensure the electrical connections.

Preferably, the support of the male plug has a geometry which is complementary to that of the housing of the female socket. It can, for example, have at least two flat lateral surfaces, parallel to one another and arranged in order to cooperate with corresponding lateral surfaces of the housing.

In a preferred embodiment, this support has notches in which the contact zones are arranged, these notches delimiting radial walls interposed between the contact zones in such a way as to insulate them electrically from one another.

Advantageously, the support consists of a piece which is separate from the first cable section and has a groove for receiving, by fitting together, the end zone of this first cable section containing said contact zones.

In the preferred embodiment, the body of the female socket has a first free end zone, a second end zone coupled with the second cable section and a middle zone of electrical connection, this middle zone having peripheral grooves which are intended to receive the contact elements, these peripheral grooves delimiting an axial core and radial walls interposed between the contact elements in such a way as to insulate them electrically from one another.

The body, in its second end zone, can have a bore passing through which is capable of receiving the end of the second cable section, the middle zone having at least one circulation channel, roughly parallel to the axis of the second cable section and capable of receiving the electrical wires of this cable section which are intended to be connected electrically to a contact element.

Each contact element preferably consists of a curved metallic spring blade of which one end projects in the housing and the other end is mounted integrally in the body by a connecting component, which can consist of a rivet housed in a radial bore passing through the axial core of the body. The connecting components can be hollow and serve as a wire guide for each electrical wire.

The axial core can have at least one flat part defining the bottom of a housing facing which the projecting end of the contact elements is arranged and the contact zones of the male plug.

The body can have two diametrically opposed circulation channels in which the electrical wires of the second cable section are distributed, as well as two diametrically opposed housings for receiving two male plugs connected to two electrodes. In this case, the contact elements provided in the two housings can be alternating every other one between the two housings.

In the preferred embodiment, the means of tightening include an electrically insulating tightening sleeve, which is mounted on the female socket and which is axially mobile between an open position in which the tightening sleeve releases the middle zone of the body and allows positioning of the support of the male plug in the corresponding housing, and a closed position in which it covers this middle zone and exerts a radial pressure on the support in its housing pressing the contact zones on the contact elements by elastically deforming them. At least the end of the tightening sleeve opposite from the stop device can have an interior bevel capable of cooperating with corresponding bevels provided on the support of the male plug when the tightening sleeve goes from its open position to its closed position, in order to facilitate sliding.

The connector can have a stop device mounted integrally on the second cable section and arranged at a distance such that it delimits the course of travel of the tightening sleeve in open position.

The connector can also have at least one electrically insulating guard interposed between the body and the tightening sleeve and arranged in order to hide at least the opening of the circulation channel made in the body and to isolate the electrical wires from people. This guard can consist of a half shell mounted on the body by nesting on the middle zone between the two end zones of the body.

In the preferred embodiment, the body and the tightening sleeve are roughly cylindrical, the interior diameter of the tightening sleeve preferably being roughly equal to the sum of the exterior diameter of the middle zone of the body and of twice the thickness of the guard, and the height of the support of said male plug is preferably at most equal to the sum of the depth of the housing and of the thickness of the guard.

The first end zone of the body can have at least one slot in extension of the housing in order to receive the first cable section of the male plug.

BRIEF DESCRIPTION OF THE DRAWING

The present invention and its advantages will appear more clearly in the following description of an embodiment given as a non-limiting example, in reference to the appended drawings in which:

FIGS. 2A to 2D are perspective views of the male plug and female socket of the connector of FIG. 1, respectively of a male plug alone, of a female socket alone before connection, of the male plug in the female socket and of the closed connector, FIGS. 3A to 3C are top views of the female socket alone respectively according to A without tightening sleeve, according to B without tightening sleeve and a view in section according to CC with tightening sleeve.

DETAILED DESCRIPTION OF THE INVENTION

Figure 1:
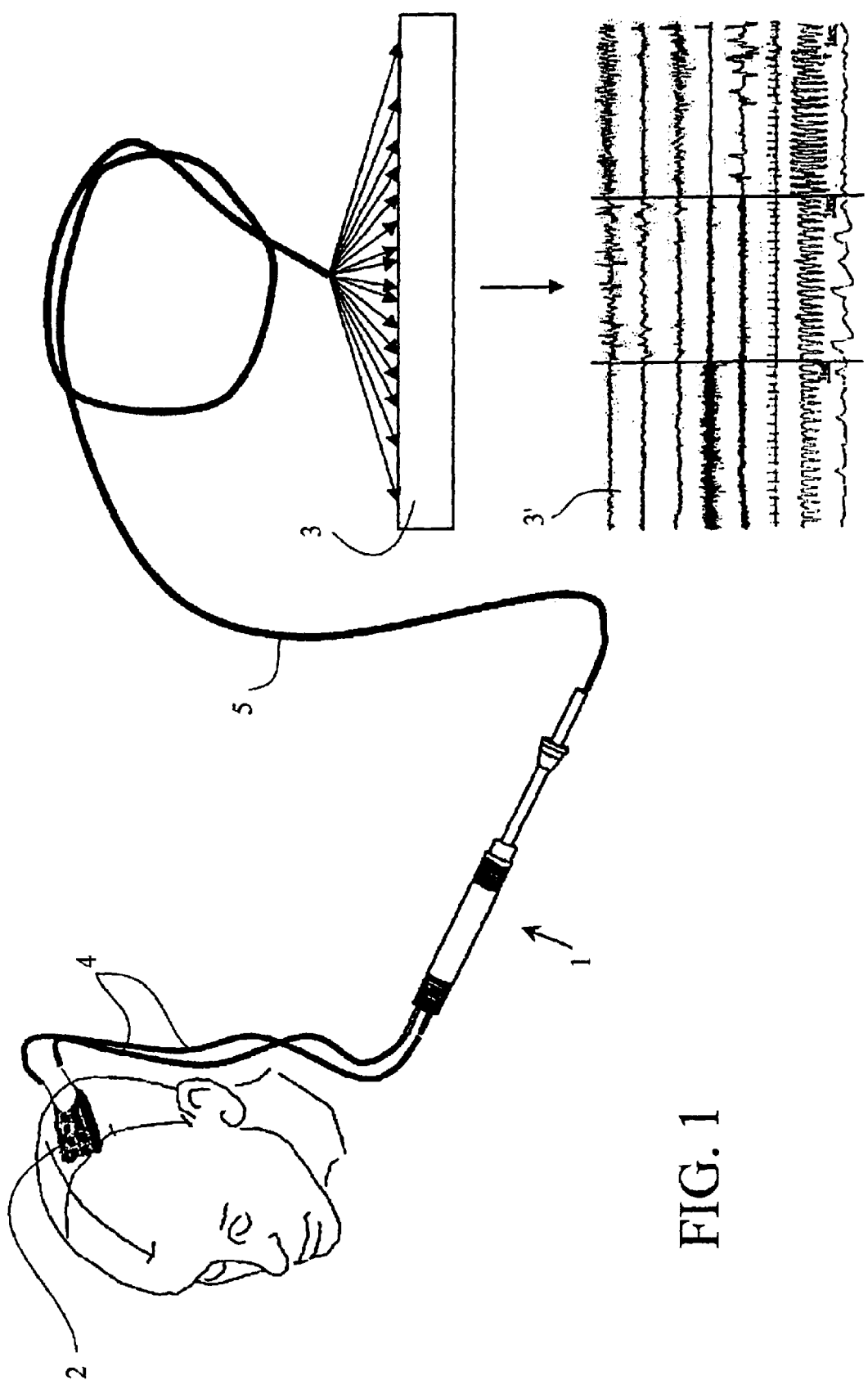
FIG. 1 represents an example of use of a connector according to the invention.

Multiple contact connector 1 according to the invention is intended to electrically connect at least one multiple contact electrode 2 to apparatus for processing 3 of the electrical signals of electrode 2. FIG. 1 illustrates an example of use of this type of electrodes 2 for a medical application. In this example, two electrodes 2, present in the form of a flat screen, are implanted in the brain of a patient and are connected to the same connector 1 by two first multiconductor cable sections 4. This connector 1 is connected to processing apparatus 3 by second multiconductor cable section 5 equipped at its free end with DIN plugs adapted connected to said processing apparatus 3. This processing apparatus 3 is, in the example, an electroencephalograph allowing one to record the cerebral activity on electroencephalogram 3'.

In reference to FIGS. 2A to 2D, connector 1 has so-called male plug 6 connected to first cable section(s) 4 and so-called female socket 7 connected to second cable section 5. Male plug 6 has elongated, electrically insulating support 60 arranged in the extension of first cable section 4 and provided, on at least one of its sides, with a number of contact zones 61 equal to the number of contacts of electrode 2, these contact zones 61 being aligned according to as line roughly parallel to the axis of first cable section 4. Female socket 7 has elongated, roughly cylindrical, electrically insulating body 70 arranged in the extension of second cable section 5 and having at least one longitudinal housing 71, roughly parallel to the axis of second cable section 5, provided with a number of contact elements 72 equivalent to the number of contact zones 61 of male plug 6. This housing 71 is capable of receiving support 60 in such a way that each contact zone 61 is arranged facing a contact element 72. Connector 1 also has tightening means 8 arranged in order to maintain support 60 in housing 71 of body 70 and to exert radial pressure on contact zones 61 and contact elements 72 so as to ensure the electrical connections.

More particularly, in reference to FIG. 2A, support 60 of male plug 6 has a geometry which is complementary to that of housing 71 provided in female socket 7 in order to allow assembling by nesting. In the example illustrated, this support 60 has a roughly parallelipiped cross section defining two lateral surfaces 60a, interior surface 60b and exterior surface 60c. The two lateral surfaces 60a are flat, parallel to one another and arranged in order to cooperate with corresponding lateral surfaces 71a of housing 71. Interior surface 60b has notches 62 in which contact zones 61 are arranged, these notches 62 delimiting radial walls 62' interposed between contact zones 61 so as to electrically insulate them from one another. This support 60 can be an integral part of first cable section 4 or can preferably consist of a separate piece. In this case, it has axial groove 63 for receiving, by fitting together, the end of this first cable section 4 containing contact zones 61.

In reference more particularly to FIGS. 3A to 3C, body 70 of female socket 7 has first free end zone 70a, second end zone 70b coupled with second cable section 5 and middle zone 70c of electrical connection. Middle zone 70c has peripheral grooves 73 which are intended to receive contact elements 72, these peripheral grooves 73 delimiting axial core 74 and radial walls 73' interposed between contact elements 72 in such a way as to insulate them electrically from one another.

Figure 4A:
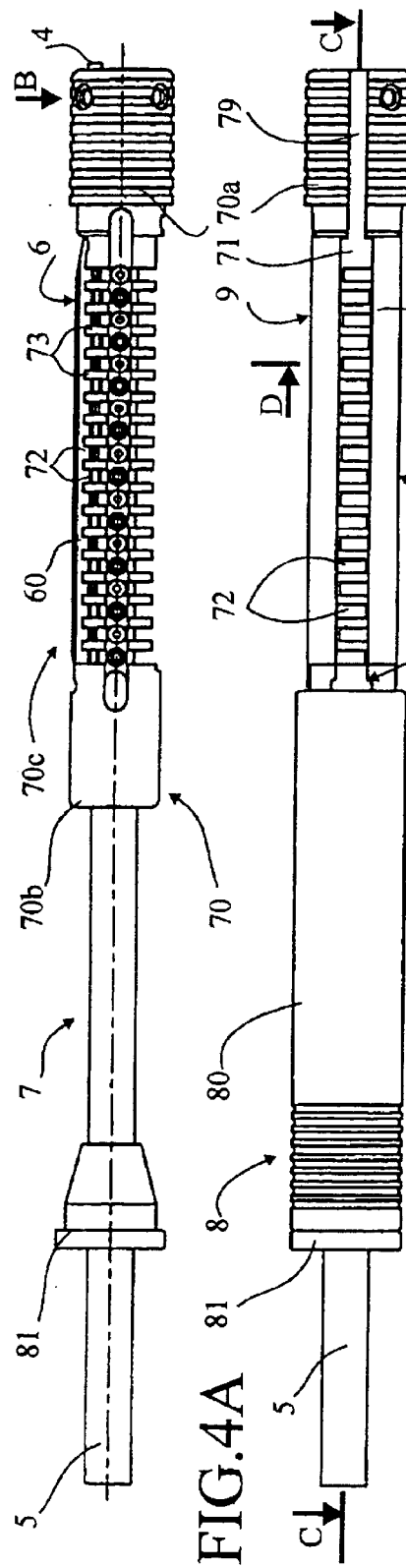
FIGS. 4A to 4D are top views of the connector respectively according to A with a male plug, without guard and without tightening sleeve, according to B without male plug, and a view in section according to CC with two male plugs and according to A with two male plugs.
Figure 4B:
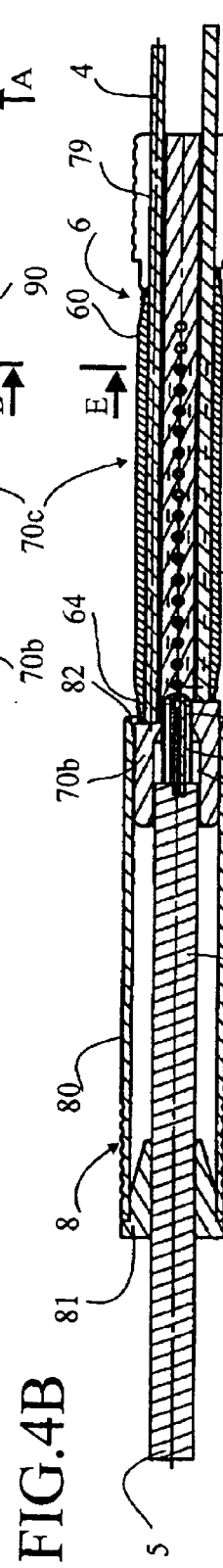
Figure 4C:
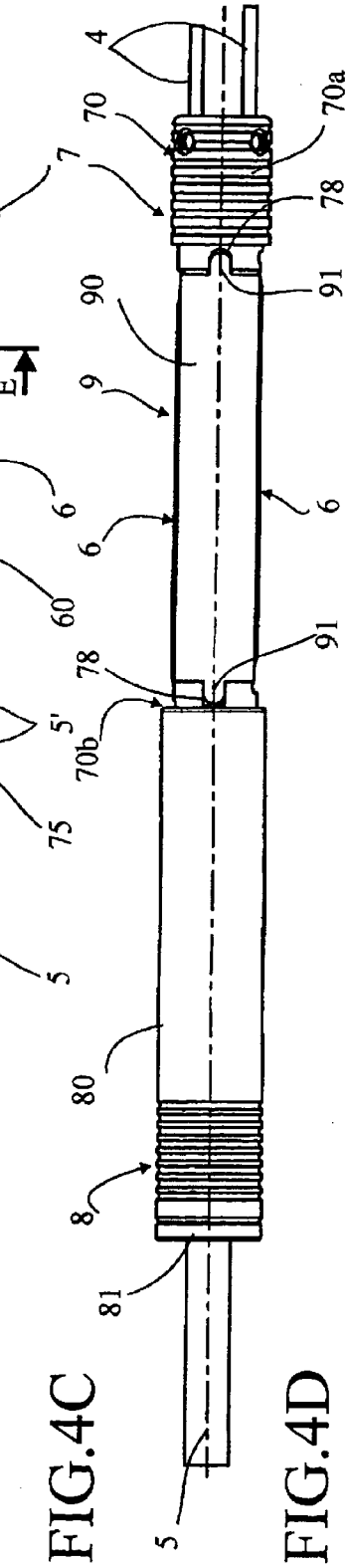
Figure 4D:
Figure 5A:
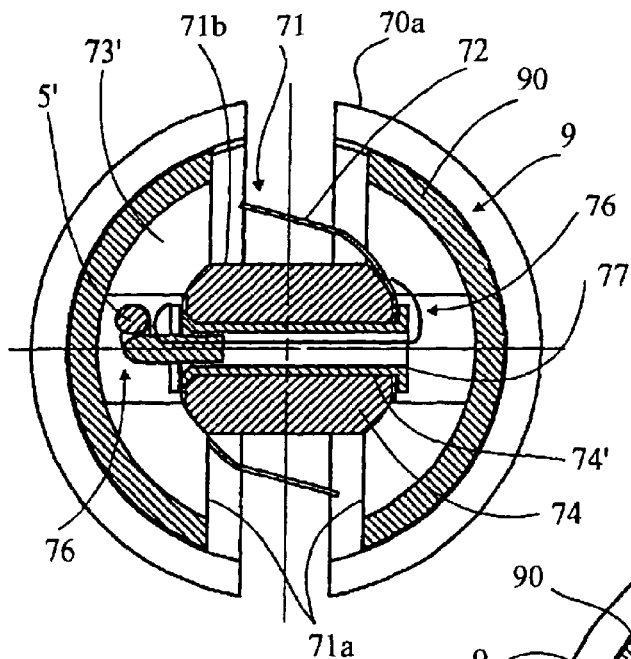
FIGS. 5A to 5C are views in radial section of the connector respectively according to DD of FIG. 4B, according to EE of FIG. 4C and according to EE of FIG. 4C with tightening sleeve.
Figure 5B:
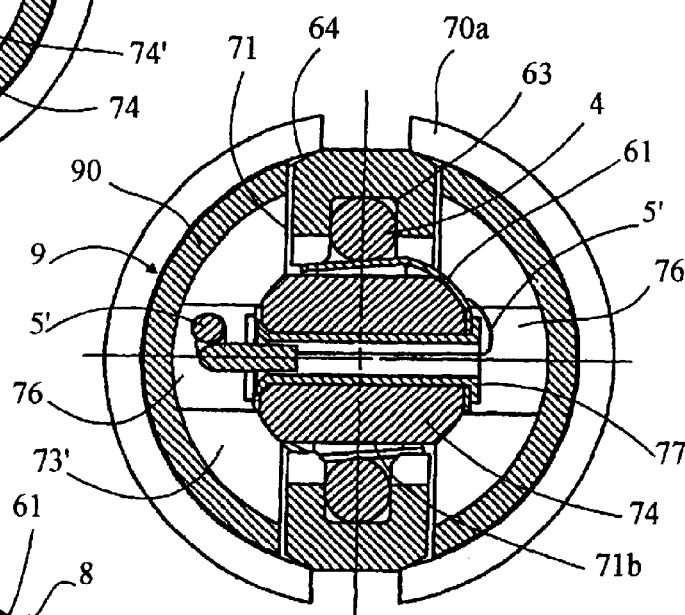
Figure 5C:
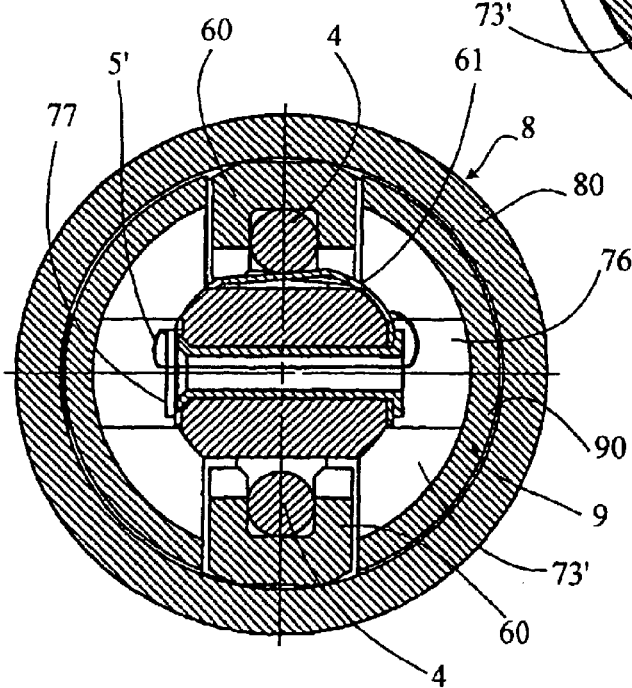

This body 70, in its second end zone 70b, has bore 75 passing through which is capable of receiving the end of second cable section 5, and in its middle zone 70c, at least one circulation channel 76, roughly parallel to the axis of second cable section 5 and capable of receiving electrical wires 5' of this cable section 5. Each electrical wire 5' is connected electrically to contact element 72 which consists of a curved metallic spring blade whose free end projects in housing 71 and of which the other end is attached on axial core 74 of body 70 by connecting component 77. In the example represented in more detail in FIG. 5A, each connecting component 77 consists of a rivet mounted through axial core 74 of body 70 through radial bore 74' and blocking the corresponding end of contact element 72 between its head and axial core 74. Each rivet 77 is hollow and serves as a wire guide for electrical wire 5' which arrives on one side of rivet 77 through circulation channel 76 and is welded on the other side to corresponding contact element 72. In the example illustrated, body 70 has two diametrically opposed circulation channels 76 in which electrical wires 5' of second cable section 5 are distributed, and two diametrically opposed housings 71 for receiving two male plugs 6 connected to two electrodes 2. Axial core 74 of body 70 has two flat parts 71b defining the bottom of housing 71 facing which the projecting parts of contact elements 72 are arranged and contact zones 61 of male plug 6. In the case of one female socket 7 for one male plug 6, contact elements 72 can be arranged staggered as illustrated in FIG. 4B. In the case of one female socket 7 for two male plugs 6, contact elements 72 can be alternating between two housings 71 as illustrated in FIG. 3B. These arrangements allow the electrical connection loads to be distributed. First end zone 70a of body 70 additionally has at least one slot 79 arranged in extension of housing 71 in order to receive first cable section 4.

Tightening means 8 include roughly cylindrical, electrically insulating tightening sleeve 80, which is mounted on female socket 7 and which is axially mobile between an open position in which it releases middle zone 70c of body 70 and allows positioning of support 60 of male plug 6 in corresponding housing 71, and a closed position in which it covers this middle zone 70c and exerts a radial pressure on support 60 which is sunken in its housing 71 pressing contact zones 61 on contact elements 72 by elastically deforming them. Stop device 81 is mounted integrally on second cable section 5, for example, by gluing, in order to delimit the course of travel of tightening sleeve 80 in open position. This stop device 81 has a truncated conical shape followed by a stop shoulder, the slope of the cone decreasing in the direction of tightening sleeve 80 in order to facilitate its fitting, and the diameter of its base being at most equal to the interior diameter of this tightening sleeve 80. The end of tightening sleeve 80 opposite from stop device 81 has interior bevel 82 which cooperates with corresponding bevels 64 provided on exterior surface 60c of support 60 in order to facilitate fitting of tightening sleeve 80 on supports 60 and the sinking of supports 60 in their housing 71.

Connector 1 according to the invention is completed by at least one electrically insulating guard 9 interposed between body 70 and tightening sleeve 80 and arranged in order to hide at least the opening of circulation channel 76 made in body 70 and to protect people from contact with electrical wires 5'. Of course, when female socket 7 is equipped with two circulation channels 76, each circulation channel 76 is covered by guard 9. Each guard 9 consists of half shell 90 and is mounted on body 70 by nesting on middle zone 70c between the two end zones 70a, 70b of body 70. In order to facilitate its positioning and to avoid positioning guards 9 on housings 71, each half shell 90 has two indexing discs 91 complementary to two notches 78 provided in end zones 70a, 70b.

In order to be able to slide tightening sleeve 80 on female socket 8, its interior diameter must be roughly equal to the sum of the exterior diameter of middle zone 70c of body 70 and of twice the thickness of guard 9. Then, in order to allow it to play its part in trapping the male plug in the female socket, the height of support 60 of male plug 6 must be at most equal to the sum of the depth of housing 71 and of the thickness of guard 9.

The use of such a connector 1 is very simple. Electrodes 2, equipped with their first cable section 4, can be implanted manually or by the intermediary of a cannula allowing their precise positioning in the zone of a patient which is to be checked or treated. After electrodes 2 have been positioned, the cannula can be withdrawn easily from the rear by sliding it along first cable section 4 and taking it out by the free end of this cable section 4 which does not hinder this. Support 60 of male plug 6 of connector 1 is then fit on the free end zone of this first cable section 4 which is housed in groove 63 provided for this purpose. This end zone has the same number of contact zones 61 as the number of electrical contacts borne by the electrode 2. These contact zones 61 can, for example, be present in the form of peripheral rings. In order to connect one or two electrodes 2 to apparatus for processing 3 of the electrical signals, one uses second cable section 5, called extension cord or adaptor, equipped on one side with female socket 7 of connector 1 and on the other side with DIN plugs.

Before this connection and in reference to FIGS. 3A to 3C and 5A, one executes the electrical connection between electrical wires 5' of second cable section 5 and contact elements 72 of the female socket. To do this, a curved spring blade is placed in each peripheral groove 73, and it is attached on axial core 74 of body 70 using rivet 77 through bore 74'. The spring blade of contact element 72 is placed in such a way that its stationary part is arranged in the bottom of circulation channel 76 and its elastically deformable free part projects in housing 71. One then introduces the free end of second cable section 5 into bore 75 of second end zone 70b of body 70 after having withdrawn the exterior insulating sheath; then, one distributes electrical wires 5' in circulation channels 76. The end of each electrical wire 5' is then stripped, introduced through rivet 77 and then welded to corresponding contact element 72 according to a predefined order. This assembling process makes it possible to provide electrical insulation between the different electrical wires 5' without risk of accidental contact with the neighboring electrical wires 5'. At the end of the electrical connection, one places guards 9 on circulation channels 76 in order to keep people from touching electrical wires 5' and so as to leave only housings 71 and contact elements 72 accessible. The assembly of female socket 70 is also protected by tightening sleeve 80.

In order to execute the connection of connector 1, in reference to FIGS. 4A to 4D, 5B and 5C, one disengages housings 71 of female socket 70 by axially moving tightening sleeve 80 in the direction of its stop device 81. One fits one or two male plugs 6 in corresponding housings 71, with it possible for first cable sections 4 to be housed in slots 79 provided for this purpose in first end zone 70a of body 70 of female socket 7. This arrangement makes it possible to guarantee the linearity of contact zones 61 of male plug 6.

Support 60 of each male plug 6 is therefore freely fit in one of housings 71 of female socket 7, contact zones 61 being in contact on contact elements 72. Then, one moves tightening sleeve 80 axially in the direction of first end zone 70a in order to cover middle zone 70c and supports 60. During its sliding, tightening sleeve 80 exerts a certain radial stress on each support 60 which is sunken in its housing 71, and contact zones 61 elastically deform corresponding contact elements 72 thus ensuring a good, entirely secured electrical connection.

INDUSTRIAL APPLICATION POSSIBILITIES

It appears clearly from this description that multiple contact connector 1 according to the invention makes it possible to attain all the aims which were set. Because of its design in the form of a cylinder and "axial" connection, it occupies a very limited volume, is lighter in weight, offers non-aggressive shapes and is much better tolerated by the patient. It is also simple to manipulate and provides a quality electrical connection, in complete safety without risk of accidental disconnection during movement of the patient, for example. It also allows the use of cannulas for implantation of electrodes 2, with it possible for male plug 6 to be disconnected easily from first cable section 4. For the same space requirement, it allows the connection of two multiple contact electrodes 2.

The present invention is not limited to the embodiment example which has been described but extends to any modification and variant obvious to the expert in the field while remaining in the range of the protection defined in the appended claims.

What is claimed is:

1. A multiple contact connector comprising:
    a) at least one male plug (6) with each male plug (6) comprising an elongated and electrically insulated support (60) and having a number of electrically conductive contact zones (61), on at least one side thereof, along a longitudinal axis of the support (60);
    b) a female socket (7) comprising an elongated and electrically insulated body (70) having at least one longitudinal and electrically insulated housing (71), on at least one side thereof, along a longitudinal axis of the body;
        wherein the housing (71) further comprises a number of electrically conductive contact elements (72) positioned along a longitudinal axis of the housing;
    c) the support (60) of the male plug (6) has notches (62) in which the contact zones (61) are arranged, the support and the notches having a geometry which is complementary to that of the housing (71) of the female socket (7) allowing assembling with one another by nesting;
    d) the contact zones (61) and the contact elements (72) face one another so that when the support (60) is nested with the housing (71), the contact zones (61) contact with the contact elements (72) and form electrical connections; and
    e) a tightening device (8), axially slidable along an exterior of the body (70) of the female socket (7), for maintaining the support (60) in the housing (71) and exerting a radial pressure on the support (60) and the contact zones (61) into electrical engagement with the contact elements (72).

2. The connector of claim 1, wherein the support (60) has at least two flat lateral surfaces (60a) while the body (70) comprises at least two lateral surfaces (71a) of the housing (71), and the flat lateral surfaces (60a) of the support (60) correspond geometrically to the lateral surfaces (71a) of the body (70).

3. The connector of claim 1, wherein, the notches (62) define radial walls (62') interposed between the contact zones (61) to electrically insulate the contact zones (61) from one another.

4. The connector of claim 1, wherein the support (60) comprises a groove (63) for receiving a first cable section (4), which contains the contact zones (61).

5. The connector of claim 1 wherein the body (70) of the female socket (7) has a first free end zone (70a), a second free end zone (70b) for coupling with a second cable section (5), and a middle zone (70c) including the housing (71), the middle zone (70c) comprises radial walls (73') interposed along the longitudinal axis of the body (70) and electrically insulate the contact elements (72) from one another.

6. The connector of claim 5, wherein the second end zone (70b) has a bore (75) for receiving an end of the second cable section (5), the middle zone (70c) has at least one circulation channel (76) parallel to an axis of the second cable section (5) for receiving electrical wires (5') of the cable section (5), the electrical wires (5') are electrically connected to the contact elements (72).

7. The connector of claim 1, wherein each contact element (72) comprises a curved metallic spring blade, a first end of each contact element (72) projects into the housing (71) and a second end of each contact element (72) is mounted integrally in the body (70) by a connecting component (77).

8. The connector of claim 7, wherein the connecting component (77) is a metallic rivet housed in a radial bore (74'), the radial bore (74') passes through an axial core (74) of the body (70).

9. The connector of claim 7, wherein the connecting component (77) is a hollow wire guide for electrical wires (5').

10. The connector of claim 8, wherein the axial core (74) of the body (70) has at least one flat part (71b) defining the bottom of the housing (71), on which a projecting end of the contact elements (72) and the contact zones (61) of male plug (6) are arranged.

11. The connector of claim 6, wherein the body (70) has two diametrically opposed circulation channels (76) in which the electrical wires (5') of the second cable section (5) are distributed.

12. The connector of claim 11, wherein the body (70) has first and second diametrically opposed housings (71) for receiving first and second male plugs (6) connected to first and second electrodes (2).

13. The connector of claim 12, wherein the contact elements (72) of the two housings (71) alternate with respect to their positions.

14. The connector of claim 5, wherein the tightening device (8) further comprises an electrically insulating tightening sleeve (80), the tightening sleeve (80) is mounted on the female socket (7) and is movable along the longitudinal axis of the body (70), between an open position and a closed position, in the open position the tightening sleeve (80) releases the middle zone (70c) of the body (70) and allows positioning of the support (60) of the male plug (6) in the corresponding housing (71), in the closed position the tightening sleeve (80) covers the middle zone (70c) and exerts a radial pressure on the support (60) in the housing (71) by pressing the contact zones (61) on the contact elements (72).

15. A multiple contact connector comprising:
    a) a male plug (6), comprising an elongated and electrically insulated support (60) formed integral with the male plug (6), and having the male plug (6) a number of electrically condutive contact zones (61), on at least one side thereof, along a longitudinal axis of the support (60);

b) a female socket (7), comprising an elongated and electrically insulated body (70) having at least one longitudinal and electrically insulated housing (71), on at least one side thereof, along a longitudinal axis of the body, the housing (71) further comprises a number of electrically conductive contact elements (72) positioned along the longitudinal axis of the housing;

c) the support (60) of the male plug (6) has notches (62) in which the contact zones (61) are arranged, the support and the notches having a geometry which is coplementary to that of housing (71) of the female socket (7), allowing assembling by mating with one another;

d) the contact zones (61) and the contact elements (72) face one another so that, when the support (60) is mated with the housing (71), the contact zones (61) contact with the contact elements (72) and form electrical connections;

e) a tightening device (8), axially slidable along an exterior of the body (70) of the female socket (7), for retaining the support (60) in the housing (71) and exerting a radial pressure on the contact zones (61) and thus on the contact elements (72) to ensure electrical connection therebetween.

16. The connector of claim 15, wherein the tightening device (8) further comprises an electrically insulating tightening sleeve (80), the tightening sleeve (80) mounted on the female socket (7) is movable along the longitudinal axis of the body (70) between an open position and a closed position, in the open position the tightening sleeve (80) releases the housing (71) of the body (70) and allows positioning of the support (60) of the male plug (6) in the housing (71), in the closed position the tightening sleeve (80) covers the housing (71) and exerts a radial pressure on the support (60) in the housing (71) by pressing the contact zones (61) on the contact elements (72).

17. The connector according to claim 14, further comprising a stop device (81) on a second cable length (5) is positioned at a distance such that the stop device (81) delimits a stoke of the tightening sleeve (80) in open position.

18. The connector according to claim 17, wherein a first end of the tightening sleeve (80) opposite the stop device (81) comprises an interior bevel (82) which cooperates with a corresponding bevel (64) on the support (60) of the male plug (6) when the tightening sleeve (80) passes from the open position to the closed position.

19. The connector according to claim 6, further comprising an electrically insulating guard (9) between the body (70) and the tightening sleeve (80) and arranged to hide an opening of the circulation channel (76) made in the body (70).

20. The connector according to claim 19, wherein the guard (9) consists of a half shell (90), the half shell (90) is positioned on the body (70) in the middle zone (70c) between the first and second free end zones (70a, 70b) of the body (70).

21. The connector according to claim 20, wherein the body (70) and the tightening sleeve (80) are approximately cylindrical, an interior diameter of the tightening sleeve (80) is approximately equal to a sum of an exterior diameter of the middle zone (70c) of the body (70) and twice a thickness of the guard (9), a height of the support (60) of the male plug (6) is at most equal to a sum of a depth of the housing (71) and thickness of the guard (9).

22. The connector according to claim 5, wherein the first free end zone (70a) of the body (70) comprises a slot (79) extending from the housing (71), the slot (79) receiving the first cable length (4) of the male plug (6).

* * * * *